United States Patent [19]
Hattori et al.

[11] Patent Number: 5,993,367
[45] Date of Patent: Nov. 30, 1999

[54] METHOD AND SYSTEM FOR THE DETERMINATION OF A QUALITY OF BONDED AREA IN A BOXMAKING BLANK

[75] Inventors: Koji Hattori; Yasuyuki Baba; Yasunari Suzuki, all of Hiroshima-ken, Japan

[73] Assignee: Mitsubishi Heavy Industries, Ltd., Tokyo, Japan

[21] Appl. No.: 09/112,357

[22] Filed: Jul. 9, 1998

[30] Foreign Application Priority Data

Jul. 15, 1997 [JP] Japan .................................. 9-189815

[51] Int. Cl.⁶ .............................. B31B 1/00; B32B 31/00
[52] U.S. Cl. ................................ 493/12; 493/15; 493/19; 156/64; 156/378; 73/865.8
[58] Field of Search .................... 493/10, 11, 12, 493/13, 14, 15, 18, 19, 25; 53/67, 69, 504; 73/865.8; 156/64, 378, 363

[56] References Cited

U.S. PATENT DOCUMENTS

| | | |
|---|---|---|
| 3,187,185 | 6/1965 | Milnes . |
| 4,704,034 | 11/1987 | Takenaka et al. . |
| 4,929,843 | 5/1990 | Chmielewski, Jr. et al. . |
| 5,059,164 | 10/1991 | Van Davelaar ............................ 493/12 |
| 5,162,873 | 11/1992 | Burk . |
| 5,212,656 | 5/1993 | Clary et al. ................................ 493/12 |

FOREIGN PATENT DOCUMENTS

| | | |
|---|---|---|
| 0 289 084 | 11/1988 | European Pat. Off. . |
| 0 902 2464 | 1/1997 | European Pat. Off. . |
| 1-214743 | 8/1989 | Japan . |
| 1-267404 | 10/1989 | Japan . |
| 5-5608 | 1/1993 | Japan . |
| 5-188003 | 7/1993 | Japan . |
| 7-12537 | 1/1995 | Japan . |
| 7-5242 | 1/1995 | Japan . |
| 9-22464 | 1/1997 | Japan . |

OTHER PUBLICATIONS

Office Action of Feb. 23, 1999 concerning the basic Japanese patent application No. HEI–9–189815(in the Japanese language).

*Primary Examiner*—John Sipos
*Assistant Examiner*—Steven Jensen
*Attorney, Agent, or Firm*—Armstrong, Westerman, Hattori, McLeland and Naughton

[57] ABSTRACT

A method and system for determining the bonding quality of a bonded area of a flapped boxmaking blank in a boxmaking apparatus at an assembling station of a production line, where opposite end portions of the blank are bonded together with confronting edges of companion end flaps defining a required gap, in terms of the outline of the gap. The quality determination is accomplished by irradiating sheetlike light onto the bonded area across the gap, forming an image of the irradiated light as a light image line composed of discrete segments which are arranged along a reference line for the flap portions and include at least one line segment located off the reference line, computing a ratio of a length of the off-line segment to the entire length of the light image line to obtain a width of the gap, and comparing the width of the gap with a preset reference value.

13 Claims, 12 Drawing Sheets

METHOD AND SYSTEM FOR THE DETERMINATION OF A QUALITY OF BONDED AREA IN A BOXMAKING BLANK

BACKGROUND OF THE INVENTION a) Field of the Invention

This invention relates to a method and system for the determination of a quality of a bonded area in a boxmaking blank with opposite end portions thereof bonded together at the bonded area. In a boxmaking apparatus for continuously assembling boxes from such blanks, the above method and system makes, based on a width of a gap formed in the bonded area of the boxmaking blank, a determination as to whether the bonded area is good or bad.

b) Description of the Related Art

In a boxmaking process for producing boxes (corrugated fibreboard containers) from corrugated cardboard blanks (corrugated fibreboard blanks), it has been the conventional practice to fold each corrugated cardboard blank of a predetermined size, which includes slots formed therein and carries ruled lines, prints and the like applied thereon, to apply a glue on an overlap formed on one of opposite end portions of the corrugated cardboard blank and then to bond the opposite end portions together via the glued overlap, all by a folder gluer.

After the corrugated cardboard blanks already folded and bonded by the folder gluer are corrected in squareness at a squaring unit, they are fed out box after box from a lower part of the squaring unit to a counter unit, where they are bundled in a desired number per bundle and are then ejected.

As is shown in FIG. 13A, for example, each corrugated cardboard blank 1 is provided with gaps 1D in parts of a top flap 1A and bottom flap 1B, respectively, at locations corresponding to a bonded area 1C between opposite end portions of the blank. It is to be noted that, concerning the bonded area 1C and the gaps 1D, the overlapping back-side blank is shown with a portion thereof cut away in FIG. 13B because the bonded area 1C and the gaps 1D are located on the back side of the bonded blank and are hardly visible.

Upon bonding the corrugated cardboard blank at the area 1C, control is performed so that, as is illustrated in FIGS. 13A and 13B, width a,b of the gaps 1D have a predetermined constant value. Namely, production of a corrugated cardboard box of an accurate shape free of off-squareness requires to bond opposite end portions of a blank together in a proper positional relationship. Whether the bonded area of the blank is good or bad can be determined depending on the width of the gap corresponding to the bonded area. It is therefore important to control the gap at a predetermined width.

Attempts have therefore been made to measure the width of such gaps in an automated contactless manner in the course of boxmaking. For example, Prime Technology Inc., Maryland, U.S.A. has already commercialized a system under the name of "Gap Watch system". Further, JP kokai 9-22464 discloses a gap quality determination system making use of a CCD (charged coupled device) camera.

According to such conventional technology, a still image of a bonded area is formed by using a stroboscope or the electronic shutter function of a CCD camera and is then subjected to so-called image processing to extract necessary information.

Described specifically, the system disclosed in JP kokai 9-22464 forms a varied-density image of the bonded area and, based on differences in density, detects edges in the bonded area and determines the width of the gap in the bonded area. In other words, when light is irradiated onto a corrugated cardboard blank, stronger reflection of light is available from a gap-free area of a corrugated cardboard blank, while weaker reflection of light is obtained from its gap-containing area. This system therefore detects a gap by making use of this difference in the intensity of reflection of light occurred for the existence and non-existence of the gap.

However, an attempt to detect a gap from a varied-density image of a bonded area of a corrugated cardboard blank involves a potential problem that, when there is a print on a surface of the corrugated cardboard blank, the printed area may also be extracted erroneously as a gap depending on the color of the print because the printed area is also different in color density and hence in the intensity of reflection of light from a ground color of (a color of a liner on) the corrugated cardboard blank. Accordingly, this system must further perform accurate distinction of a true gap from the gap information so obtained.

Further, the liner color is available with considerably wide variations in color tone, ranging from a very light tone called "white liner" to a significantly dark tone called "K liner". This may result in a variation in the quantity of reflection of light from the surface of a liner in a gap and hence in the density of the surface of the liner in the gap, thereby possibly making it difficult to accurately discriminate a difference from the density of the gap. As a consequence, the measurement of the width of a gap in a bonded area, said measurement performing image processing such as edge extraction by using a varied-density image of the bonded area, has difficulty in making determination at high reliability.

SUMMARY OF THE INVENTION

An object of the present invention is to provide, by an improvement on the manner of formation of an image of the bonded area in a boxmaking blank, a method for the determination of a quality of a bonded area in a boxmaking blank, which permits an easy determination as to whether the bonded area is good or bad.

Another object of the present invention is to provide, by an improvement on the manner of formation of an image of the bonded area in a boxmaking blank, a system for the determination of a quality of a bonded area in a boxmaking blank, which permits an easy determination as to whether the bonded area is good or bad.

To achieve these objects, a method and system according to the present invention for the determination of a quality of a bonded area in a boxmaking blank have characteristic features to be described hereinafter.

Namely, the method according to the present invention is provided for the determination of a quality of a bonded area in a boxmaking blank with opposite end portions thereof bonded together at the bonded area. The method is suited for application to a boxmaking apparatus adapted to continuously assemble boxes from such boxmaking blanks. The method includes irradiating light from a light source onto the bonded area of the blank travelling on and along a production line, forming an image of the bonded area by image pick-up means, computing a width of a gap formed in the bonded area on a basis of information of the image so formed, and from the results of the computation, making a determination as to whether the bonded area is good or bad. The light is irradiated in the form of a sheet from the light source toward the bonded area so that the sheetlike light extends across the gap. The image pick-up means is arranged with an image pick-up direction thereof extending at an angle relative to a direction of an optical axis of the sheetlike light from the light source, and an image of the bonded area irradiated by the sheetlike light from the light source is formed by the image pick-up means so arranged. The width of the gap in the bonded area is computed based on information of the image formed by the image pick-up means so arranged. The results of the computation are then compared with a preset upper limit and lower limit to determine whether the bonded area is good or bad.

Owing to the above-described characteristic features, the method of the present invention can easily measure the bonded area in the blank irrespective of the density, and can also easily measure the bonded area in the blank without being affected by the color of a liner or a printed area on the blank. This method therefore has an advantage that the performance and reliability of a boxmaking line making use of such blanks can be substantially improved.

In the above-described method for the determination of the quality of the bonded area in the boxmaking blank, before the irradiation of the sheetlike light from the light source and the subsequent formation of the image by the image pick-up means, the light source and the image pick-up means may be adjusted in position so that the light source and the image pick-up means are directed toward a position of the bonded area of the blank travelling on and along the production line.

Further, the computation of the width of the gap in the bonded area, the computation being conducted based on the information of the image formed by the image pick-up means, may be conducted by a projection method or a sequential comparison method.

In addition, the system according to the present invention is provided for the determination of a quality of a bonded area in a boxmaking blank with opposite end portions thereof bonded together at the bonded area. The system is suited for arrangement in association with a boxmaking apparatus adapted to continuously assemble boxes from such boxmaking blanks, whereby a width of a gap formed in the bonded area of the blank is measured to determine whether the quality of the bonded area is good or bad. The system comprises a light source for irradiating light in the form of a sheet toward the bonded area travelling on and along a production line so that the sheetlike light extends across the gap; image pick-up means for forming an image of the bonded area irradiated by the sheetlike light from the light source, the image pick-up means being arranged with an image pick-up direction thereof extending at an angle relative to a direction of an optical axis of the sheetlike light from the light source; and computation and determination means for computing the width of the gap in the bonded area on a basis of information of the image from the image pick-up means and comparing the results of the computation with a preset upper limit and lower limit to determine whether the bonded area is good or bad.

Owing to the above-described characteristic features, the system of the present invention can easily measure the bonded area in the blank irrespective of the density, and can also easily measure the bonded area in the blank without being affected by the color of a liner or a printed area on the blank. This system therefore has an advantage that the performance and reliability of a boxmaking line making use of such blanks can be substantially improved.

The above-described system for the determination of the quality of the bonded area in the boxmaking blank may further comprise a positioning device for setting states of arrangement of the light source and the image pick-up means in correspondence with a position of the bonded area of the blank travelling on and along the production line.

In the above-described system for the determination of the quality of the bonded area in the boxmaking blank, the computation and determination means may compute the width of the gap by the projection method or the sequential comparison method on the basis of the information of the image from the image pick-up means.

In the above-described system for the determination of the quality of the bonded area in the boxmaking blank, the light source and the image pick-up means may be suited for arrangement above or below the production line, and additional light source and image pick-up means as defined above may be included for arrangement below or above the production line so that the additional light source and image pick-up means are located on a side opposite to the light source and the image pick-up means with respect to the production line.

In the above-described system for the determination of the quality of the bonded area in the boxmaking blank, the blank may travel with a widthwise direction of the gap directed at a right angle relative to or in parallel with a longitudinal direction of the production line.

DETAILED DESCRIPTION OF THE PREFERRED EMBODIMENT

With reference to the drawings, a description will hereinafter be made about the construction of the system according to the preferred embodiment of the present invention for the determination of the quality of the bonded area in the boxmaking blank.

Figure 2:
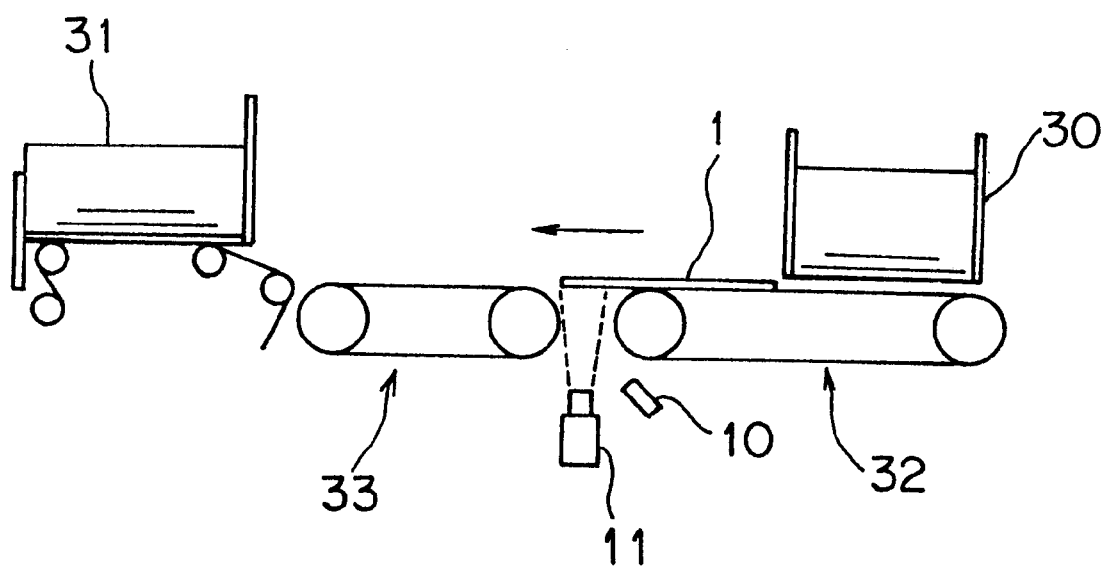
FIG. 2 is a diagram illustrating an installation position of the system according to the embodiment of the present invention for the determination of a quality of a bonded area in a boxmaking blank.

As is illustrated in FIG. 2, the system according to this embodiment for the determination of the quality of the bonded area of the boxmaking blank is provided with the light source 10 having an optical axis and the photosensor 11, and these light source 10 and photosensor 11 are arranged between a squaring unit 30 and a counter unit 31 disposed in a boxmaking production line for corrugated cardboard boxes.

Namely, each corrugated cardboard blank 1 as a material for the corrugated cardboard box is bonded at opposite end portions thereof and, subsequent to correction into a square form at the squaring unit 30, the corrugated cardboard blank 1 is transported to the counter unit 31. At this time, the corrugated cardboard blank 1 is fed out from a lower part of the squaring unit 30 and is then transported to the counter unit 31 (in the direction of a leftward arrow in FIG. 2) by a first conveyor 32 and a second conveyor 33.

The first conveyor 32 and the second conveyor 33 are arranged with an interval left therebetween, and the light source 10 and photosensor 11 of the system are arranged below a transport line between the first conveyor 32 and the second conveyor 33.

Figure 1:
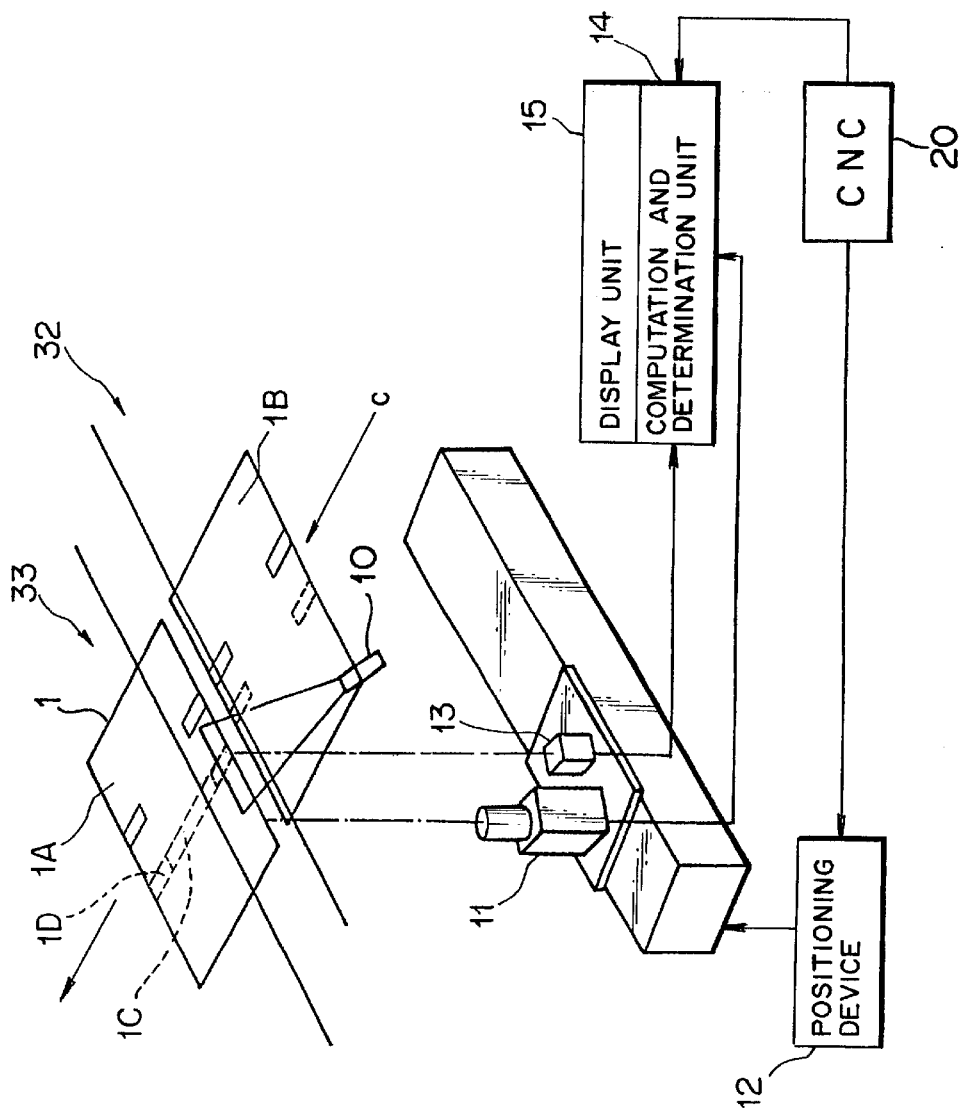
FIG. 1 is a simplified block diagram of a system according to a preferred embodiment of the present invention for the determination of a quality of a bonded area in a boxmaking blank.

In addition to the light source 10 and the photosensor 11, the system for the determination of the quality of the bonded area in the boxmaking blank is also provided, as is shown in FIG. 1, with a positioning device 12, a blank pass detection sensor 13, a computation and determination unit 14 and a display unit 15. The positioning device 12 and the computation and determination unit 14 are controllable by a computer numerical control (CNC) 20 of the boxmaking apparatus.

Here, the corrugated cardboard blank 1 is transported in the direction of arrow C on and along the production line with a top flap 1A and a bottom flap 1B directed forward and rearward, respectively, and with a bonded area 1C facing downward. The light source 10 irradiates sheetlike light (sectorally-flaring laser beam) onto the gap 1D in the bonded area 1C of the corrugated cardboard blank 1, which is travelling on and along the production line, so that the sheetlike light is directed extending across the gap 1D. In FIG. 1, the direction of the sheetlike light from the light source 10 is not set in a direction perpendicular to a lower side of the corrugated cardboard blank 1 but is set in a direction aslant relative to the travelling direction of the corrugated cardboard blank 1 as indicated by arrow c.

Incidentally, the sectorally-flaring laser beam is used as the light source 10 as mentioned above. Besides such a laser beam, it is also possible to use a strong sheetlike light source constructed of a strong metal halide light source, a cylindrical lens and the like.

Further, the photosensor (camera) 11 as the image pick-up means is adapted to form an image of the bonded area 1C irradiated by the sheetlike light from the light source 10. It forms the image of the bonded area 1C at a timing corresponding to a detection signal by the blank pass detection sensor 13 to be described subsequently herein. As is illustrated in FIG. 2, the photosensor is arranged in a direction perpendicular to the corrugated cardboard blank 1. The photosensor 11 shown in FIG. 2 will hereinafter be called the "camera" as it is constructed of a matrix-array CCD camera.

Although the camera 11 is arranged with its image-forming direction toward the corrugated cardboard blank 1 extending in a direction perpendicular to the lower side of the corrugated cardboard blank 1 in FIG. 2, this image-forming direction is not limited to such a direction. It is sufficient if the image-forming direction is set to form an angle relative to the direction of an optical axis of the sheetlike light from the light source 10.

Accordingly, the optical axis of the sheetlike light from the light source 10 may extend at a right angle relative to the lower side of the corrugated cardboard blank 1 when the image-forming direction is set aslant relative to the lower side of the corrugated cardboard blank 1. By the way, these light source 10 and camera 11 are constructed integrally as a sensing device in this embodiment.

The positioning device 12 is to adjust the state of arrangement of the sensing device, which is composed of the light source 10 and the camera 11, in correspondence with the position of the bonded area 1C of the corrugated cardboard blank 1 travelling on and along the production line. This positional adjustment is effected based on a signal from the control 20 which will be described subsequently herein. Incidentally, these positioning device 12 and sensing device 10,11 make up a gap width sensor head. Further, the term "state of arrangement" as used herein means "position or location" and/or "angle or spatial position".

The blank pass detection sensor 13 detects a timing at which the sheetlike light is irradiated onto the bonded area 1C, and generates a detection signal indicative of the timing. This blank pass detection sensor detects the leading edge and trailing edge of the corrugated cardboard blank 1 while distinguishing these edges from each other. At the timing based on the detection signal from the blank pass detection sensor 13, the irradiation of the light from the light source 10 and the image formation by the camera 11 are performed.

As the blank pass detection sensor 13 is arranged on an upstream side, as viewed in the direction of transportation (see the arrow c), of the camera 11 by a predetermined distance, the detection of the trailing edge of the corrugated cardboard blank 1 by the blank pass detection sensor 13 also means the concurrent existence of the gap 1D, which is formed in the bonded area 1C on the side of the bottom flap 1B, within a detection area of the camera 11.

When the blank pass detection sensor 13 has detected the leading edge of the corrugated cardboard blank 1, however, the gap 1D in the bonded area 1C on the side of the top flap 1A has not reached yet the inside of the detection area of the camera 11. Subsequent to elapse of a predetermined time from this time point, the gap 1D on the side of the top flap 1A reaches the detection area of the camera 11. The time required from the detection of the forward edge of the corrugated cardboard blank 1 until the arrival of the gap 1D in the detection area is determined by a positional relationship between the blank pass detection sensor 13 and the camera 11, a positional relationship between the leading edge of the corrugated cardboard blank 1 and the gap 1D on the side of the top flap 1A and the traveling speed of the corrugated cardboard blank 1.

When the blank pass detection sensor 13 outputs a leading edge detection signal upon detection of the leading edge of the corrugated cardboard blank 1, the width of the gap 1D in the bonded area 1C on the side of the leading edge (on the side of the top flap 1A) is measured at a timing delayed by a predetermined time. When the blank pass detection sensor 13 outputs a trailing edge detection signal upon detection of the trailing edge of the corrugated cardboard blank 1, on the other hand, the width of the gap 1D in the bonded area 1C on the side of the trailing edge (on the side of the bottom flap 1B) is measured concurrently with the output of the trailing edge detection signal.

The computation and determination unit (good/bad determination unit) 14 computes the width of the gap 1D on the basis of the signal from the camera 11 and then compares the results of the computation with a preset upper limit and lower limit to make a determination as to whether the bonded area 1C is good or bad. The computation and determination unit is controlled by the control 20 which will be described subsequently herein. Further, the display unit (determination results display unit) 15 serves to display the results of the determination which has been made at the computation and determination unit 14.

The control (CNC) 20 controls the above-mentioned positioning device 12 and computation and determination unit 14, and is constructed as a control for the entire boxmaking apparatus. Specifically, the control 20 first performs a positional adjustment of the sensing device (the light source 10 and the camera 11) before the initiation of an operation (job) so that the light source 10 and the camera 11 can irradiate and detect the bonded area 1C of each corrugated cardboard blank 1 travelling on and along the production line.

In other words, positional information of the bonded area 1C is sent from the control 20 to the positioning device 12, and the positioning device 12 then performs positional adjustments of the light source 10 and camera 11 in accordance with the positional information so that their states of arrangement can be set corresponding to the passing position of the bonded area 1C.

After the initiation of the operation, the sheetlike light is irradiated responsive to a command signal from the control 20 from the light source 10 toward the bonded area 1C so that the sheetlike light extends across the gap 1D, an image of the bonded area 1C irradiated by the light from the light source 10 is formed by the camera 11, and the width of the gap 1D in the bonded area 1C is then computed based on information of the image formed by the camera 11. The results of the computation are compared with the preset upper limit and lower limit, whereby a determination is made as to whether the bonded area 1C is good or bad. By the way, the above-mentioned control by the control 20 is performed lot by lot.

Figure 3A:
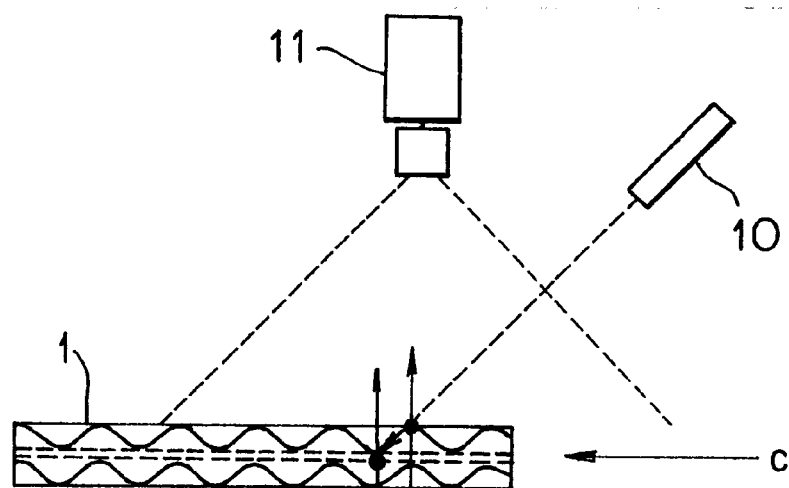
FIG. 3A is a schematic arrangement elevation of a light source and a photosensor as image pick-up means, which will be referred to upon description of the principle of detection of the width of a gap in the bonded area of the boxmaking blank by the system according to the embodiment of the present invention.
Figure 3B:
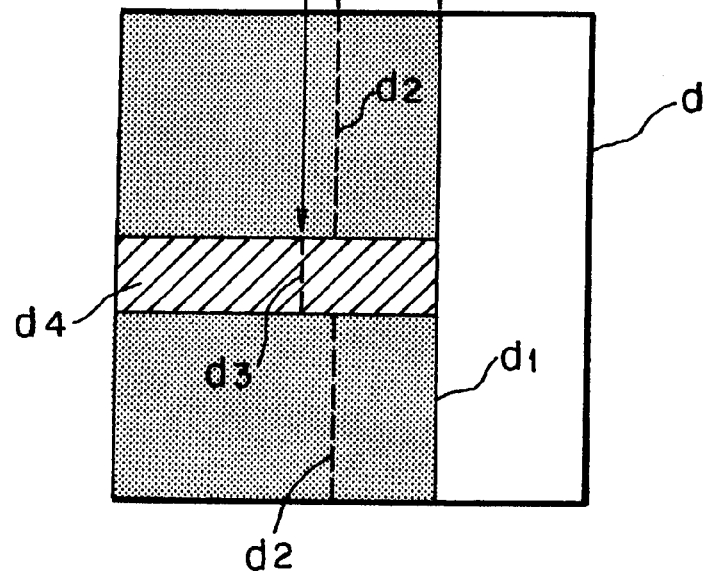
FIG. 3B is a diagram schematically showing a plan image obtained by the photosensor in the arrangement depicted in FIG. 3A.

With reference to FIGS. 3A and 3B, a detailed description will now be made about the principle of the above-mentioned detection of the width of the gap in the bonded area 1C by the light source 10 and the camera 11. It is to be noted that FIG. 3A is a diagram schematically illustrating the light source 10 and the camera 11 as viewed from the side of the conveyor line but the positions and directions of the light source 10 and camera 11 as shown in FIGS. 1 and 2 are vertically reversed in FIG. 3A.

As is depicted in FIG. 3A, when an image of the bonded area 1C irradiated at an angle by the sheetlike laser beam from the light source 10 is formed by the camera 11 arranged with its detecting direction extending at a right angle relative to the corrugated cardboard blank 1, a plan view image d is obtained at the camera 11 as shown in FIG. 3B.

Incidentally, FIG. 3B illustrates by way of example the image formed by the camera 11 in connection with the gap 1D in the bonded area 1C on the side of the trailing edge (on the side of the flap 1B) of the corrugated cardboard blank 1. In FIG. 3B, a straight line d1 indicates the trailing edge of the corrugated cardboard blank 1, dashed lines d2,d3 represent lines of light formed on the corrugated cardboard blank 1 as a result of the irradiation by the laser beam, and a region d4 with hatching designates the part of the gap 1D.

Among these, the dashed lines d2 correspond to the lines of light formed on the surface of the corrugated cardboard blank 1, while the dashed line d3 corresponds to the line of light formed at the part of the gap (the region d4 with the hatching) in the bonded area 1C. As is readily appreciated from this diagram, a difference arises in the position of a line of light between the gap part d4 and the other parts on the image d.

Reasons for the occurrence of this positional difference will be explained hereinafter with reference to FIG. 3A. In the neighborhood of the gap 1D as the detection target in the bonded area 1C of the corrugated cardboard blank 1, the gap-free part is irradiated by the light at a liner on the surface of a blank portion on a side closer to the light source 10 and the camera 11 but the gap part is irradiated by the light at a liner on the surface of a blank portion on a side farther from the light source 10 and the camera 11. A difference therefore arises in the point of irradiation by the laser beam between the gap-free parts and the gap part.

The lines of light formed at the respective parts are hence shifted from each other on the image d formed by the camera 11 from the oblique direction relative to the irradiated direction of the light.

Namely, when a sheetlike laser beam impinges an object having a concavity or convexity at a surface thereof like the corrugated cardboard blank 1 containing the gap 1D, a line of light is formed as a non-continuous line along the edge of the concavity or convexity. Making use of this characteristic phenomenon of noncontinuity, the gap part can be ascertained. This method is called the "light cutting method" and is used for the measurement of three-dimensional shapes. In this embodiment, the gap part and the other parts are discriminated from each other by using this method.

As has already been mentioned above, a similar image can also be obtained when the bonded area vertically irradiated by a sheetlike laser beam is taken by the camera 11 arranged at an upper left or right position.

A specific description will now be made about an extraction method of the gap in the bonded area 1C and a measuring method of its width.

Figures 4A, 4B:
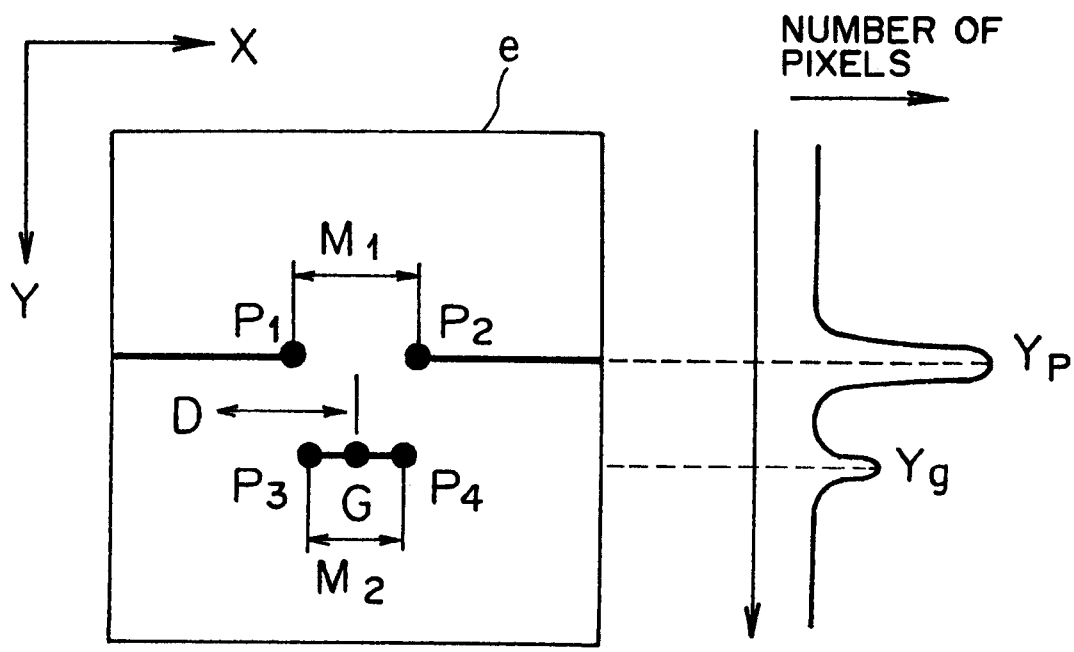
FIG. 4A is a schematic diagram of an image for describing a first detection method (projection method) as applied to the width of the gap in the bonded area of the boxmaking blank by the system according to the first embodiment of the present invention.
FIG. 4B is a schematic projection diagram obtained by projecting, in X direction, image data corresponding to the image of FIG. 4A.

When a laser beam is irradiated onto the bonded area 1C, an image e containing mutually-shifted lines of light as shown in FIG. 4A is obtained at the camera 11. As is indicated in FIG. 4A, the width of the gap in the bonded area 1C can be determined as the length M2 of a line segment $P_3$–$P_4$ or as the distance $M_1$ between points $P_1$ and $P_2$. In FIG. 4A, letter "G" indicates a barycenter of the line segment $P_3$–$P_4$ and letter "D" designates an X coordinate of the barycenter G. From the image information, the length M2 of the line segment $P_3$–$P_4$ or the distance M1 between the points $P_1$ and $P_2$ is thus determined as will be described next.

In this embodiment, the image information is first processed by the labeling method, followed by the calculation of the width of the gap by the projection method or the sequential comparison method.

(a) Processing of the image data by the labeling method:

According to the processing by the labeling method, bi-level digitization processing is first conducted, namely, individual pixels in a varied-density image formed at the camera 11 are compared pixel by pixel with a predetermined constant density level and to each pixel, 0 (black) is allotted when the density of the pixel is lower than the predetermined constant density level or 1 (white) is allotted when the density of the pixel is higher than the predetermined constant density level.

The bi-level digitized data obtained by the bi-level digitization processing are then subjected to elimination processing of isolated points and continuation processing of noncontinuous points. Subsequent to elimination of a noise and the like, labeling processing is performed further to take each continuous line as a single group. From the data so labeling processed, line segment data of the gap are extracted.

(b) Calculation of the width of the gap by the projection method (the first detection method):

According to the projection method, the bi-level digitized image data are first projected in X direction. Because each pixel has a value of 1 or 0 in the bi-level digitized image data, the values (1 or 0) of individual pixels in each row are successively added by the projection in X direction. By performing this computation over the entire rows, the numbers of pixels in the respective rows (Y coordinate points) can be determined. By conducting projection of the bi-level digitized data in X direction (in the direction of the lines of light), a maximum peak is determined from the results of this projection.

By searching the maximum peak $Y_p$ as described above, a line position at which the sheetlike light crosses the surfaces of the corrugated cardboard blank 1 can be extracted. Another search is then conducted for a peak $Y_g$ which is located at a position adjacent to the maximum peak $Y_p$. This makes it possible to extract the gap part. Namely, the width of the gap can be obtained by choosing data closer to the $Y_g$ coordinate point from the above-mentioned labeling processed segment data and determining the length of the line segment (the number of pixels).

When lines of light are horizontal, two peaks $Y_p$,$Y_g$ are obtained by adding individual pixels line after line, for example, as shown in FIG. 4B. In the diagram, the peak $Y_p$ is the maximum peak in the image e. This peak $Y_p$ indicates the results (the number of pixels) of addition of the data of the segment line passing through the point $P_1$ with the data of the segment line extending through the point $P_2$. On the other hand, the peak $Y_g$ represents the results of addition of the data of the line segment between the points $P_3$ and $P_4$, and the results of the addition correspond to the length M2 of the line segment $P_3$–$P_4$.

(c) Calculation of the width of the gap by the sequential comparison method (the second detection method):

In the projection method described above under (b), projection is conduced in X direction, a peak is detected from the results of the projection, and the width of the gap in the bonded area 1C is then determined from the height of the peak. According to the sequential comparison method, however, distances between labeling processed data of line segments and an end of an image are measured and, based on the data at which a difference arises in the distance, the width of the gap in the bonded area 1C is determined.

Figure 5:
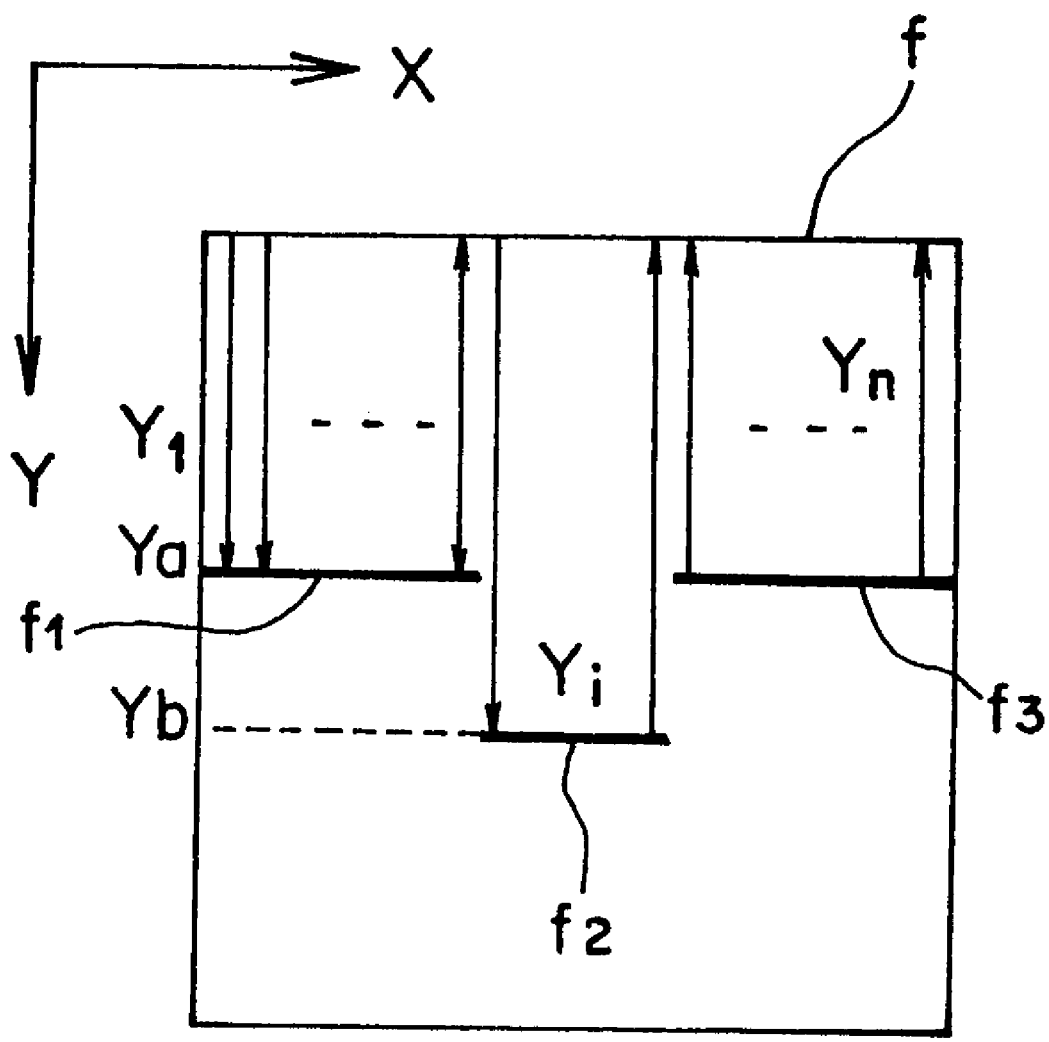
FIG. 5 is a schematic diagram of an image, which will be referred to upon description of a second detection method (sequential comparison method) as applied to the width of the gap in the bonded area of the boxmaking blank by the system according to the first embodiment of the present invention.

Described specifically, as is illustrated in an image f of FIG. 5, the distances $Y_i$ between labeling processed data of line segments ($f_1$ to $f_3$) and the end of the image f (the upper edge of the image f in FIG. 5) are used as position data of lines of light at individual X coordinate points. These distances $Y_i$ are measured in the order of pixel units ($Y_1 \rightarrow Y_n$) toward the X-axis.

In the course of this measurement ($Y_1 \rightarrow Y_n$), a difference between each position data $Y_i$ and its adjacent position data $Y_{i+1}$ is determined. Assuming that there is a continuous line segment when this difference is not greater than a predetermined value, a line segment which is not in continuation with the other line segments is formed exclusively corresponding to the gap part. If a line segment which is not in continuation with other line segments is extracted and the number of pixels in the thus-extracted line segment is determined, the number of the pixels indicates the length of the line segment, that is, the width of the gap.

Figure 6:
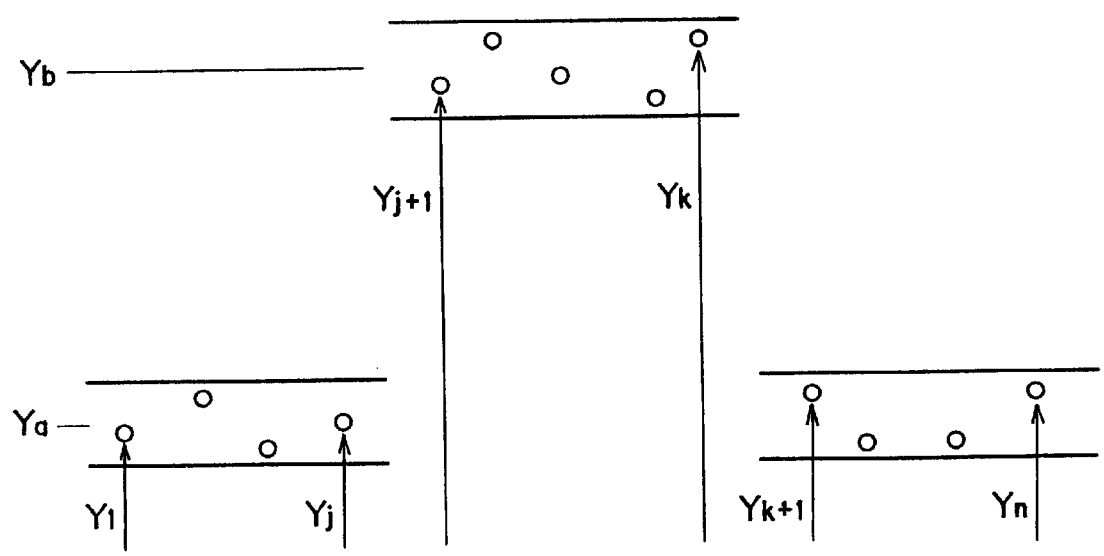
FIG. 6 is an enlarged diagram of an image obtained by using the system of the embodiment of the present invention in accordance with the second detection method.

From a theoretical standpoint, data on such distances $Y_i$ should appear as shown in FIG. 6, corresponding to lines of light at the gap-free part (see $f_1$ and $f_3$ in FIG. 5) and a line of light at the gap part (see $f_2$ in FIG. 5). It is to be noted that, compared with FIG. 5., FIG. 6 shows the lines of light upside down.

Described specifically, distances $Y_1$–$Y_j$ of a first pixel to a j-th pixel have continuity with each other (the differences between the adjacent distance data are not greater than the predetermined value) and are around $Y_a$. Between the j-th pixel and a (j+1)-th pixel, however, there is noncontinuity (the difference between the adjacent distance data $Y_j$ and $Y_{j+1}$ is greater than the predetermined value). Further, distances of the (j+1)-th pixel to a k-th pixel have continuity with each other (the differences between the adjacent distance data are not greater than the predetermined value) and are around $Y_b$. Moreover, there is noncontinuity between the k-th pixel and a (k+1)-th pixel (the difference between the adjacent distance data $Y_k$ and $Y_{k+1}$ is greater than the predetermined value), but distances $Y_{k+1}$–$Y_n$ of the (k+1)-th pixel to an n-th pixel have continuity with each other (the differences between the adjacent distance data are not greater than the predetermined value) and are around $Y_a$.

Figure 7A:
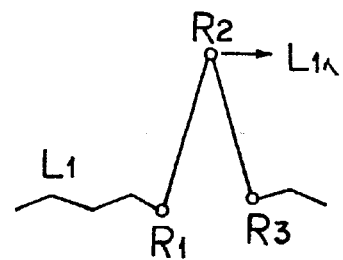
FIG. 7A is a diagram showing one example of a detection pattern of the bonded area as obtained by using the system of the embodiment of the present invention in accordance with the second detection method.
Figure 8A:
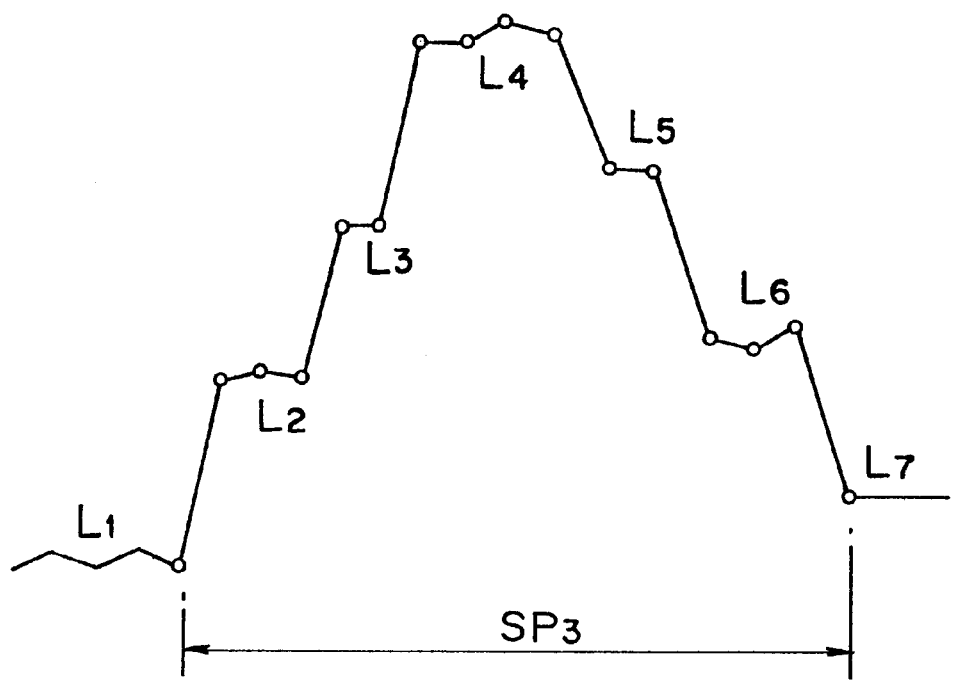
FIG. 8A is a diagram showing a still further example of the detection pattern of the bonded area as obtained by using the system of the embodiment of the present invention in accordance with the second detection method.
Figure 8B:
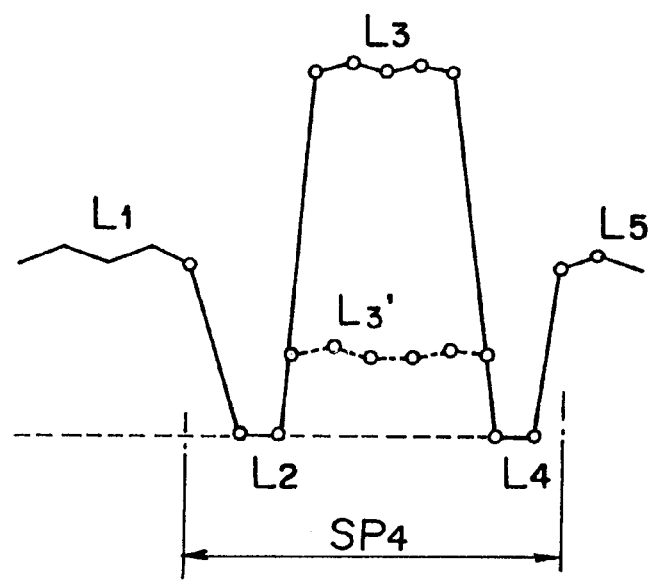
FIG. 8B is a diagram showing a still further example of the detection pattern of the bonded area as obtained by using the system of the embodiment of the present invention in accordance with the second detection method.
Figure 9:
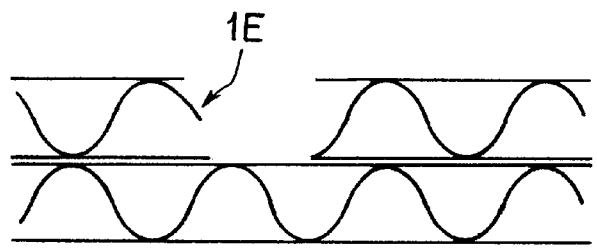
FIG. 9 is a diagram illustrating the state of a cutting failure in a core part of a corrugated cardboard blank.

Actual image data, however, do not always appear as shown in FIG. 5 due to the influence of a noise, the machined shape of such edge portions 1E of the corrugated cardboard blank 1 as shown in FIG. 9, said edge portions forming peripheral edge portions of the gap 1D, a detection failure of light by the camera 11, and/or a like cause. Likewise, distance data do not necessarily appear as illustrated in FIG. 6, due to the influence of a noise, the machined shape of the edge portions 1E of the corrugated cardboard blank 1, a detection failure of light, and/or a like cause. Instead, the data on the distances $Y_i$ are considered to appear in rather varied forms as shown in FIGS. 7A to 7C and FIGS. 8A and 8B.

Signs $L_1$–$L_7$ shown in FIGS. 7A to 7C and FIGS. 8A and 8B are labels allotted to data groups which were recognized as line segments as a result of determination of differences. Although the labels $L_1$–$L_5$ are commonly used in at least two of FIGS. 7A to 7C and FIGS. 8A and 8B, each label in one of these drawings has no relevance to the corresponding label in one or more of the remaining drawings.

The determination of continuity or noncontinuity among the distances $Y_i$ is therefore conducted with the following matters in mind.

First, a noise is dealt with. Assuming that a noise basically appears as a single-shot signal, it is designed that, upon occurrence of a noise, noncontinuity is determined to exist between a pixel detected at the time of the occurrence of the noise and each of pixels detected before and after the occurrence of the noise. As is shown in FIG. 7A, for example, if there is data $R_2$ greater than a constant value of label $L_1$ between two data $(R_1,R_2)$ determined to fall in label $L_1$, this data $R_2$ is determined to be a noise and is included in label $L_1$.

Figure 7B:
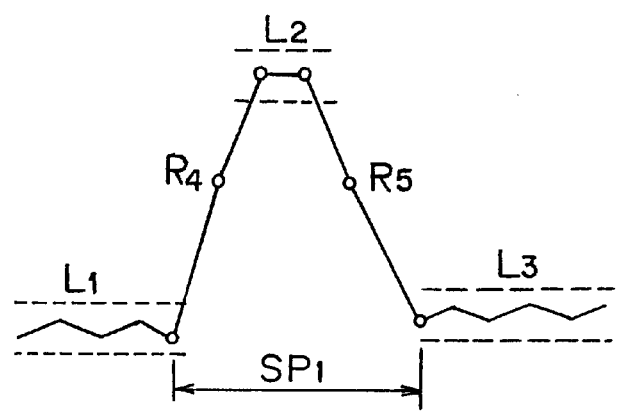
FIG. 7B is a diagram showing another example of the detection pattern of the bonded area as obtained by using the system of the embodiment of the present invention in accordance with the second detection method.

As is shown in FIG. 7B, for example, between a data group determined to be label L1 and another data group determined to be label L2, in other words, in a transition state from label L1 to label L2 or from label L2 to label L1, data $R_4$ which is remote from any of the predetermined constant values of the respective labels, is neglected. Data $R_5$ situated between label L2 and label L3 is neglected likewise.

As has been described above, a measurement data is either neglected or included in an adjacent label provided that it is not continuous with any of its adjacent data.

Figure 7C:
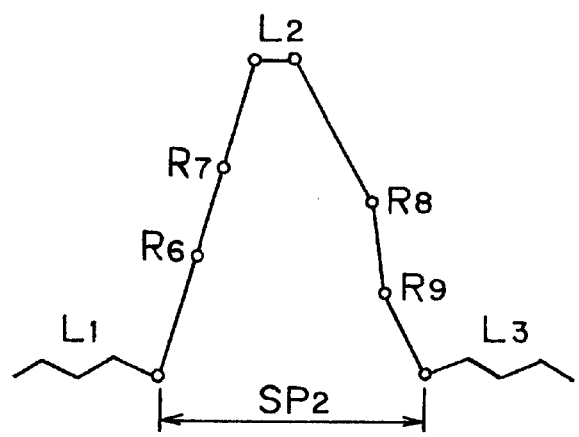
FIG. 7C is a diagram showing a further example of the detection pattern of the bonded area as obtained by using the system of the embodiment of the present invention in accordance with the second detection method.

When, as is shown in FIG. 7C, for example, two noncontinuous data $[(R_6,R_7)$ or $(R_8,R_9)]$ are successively situated between label L1 and label L2 or label L2 and label L3, these two data are not registered but are neglected as in the case of FIG. 7B because they are remote from any of the labels.

Although the two noncontinuous measurement data are successively situated in the above case, there is a difference greater than a certain constant value between the values of these two data. Accordingly, they cannot be put together in a single label and are neglected.

When data similar to those shown in the above-described FIG. 7B or 7C are obtained, the line segment data (equivalent to $f_2$ in FIG. 5) of the bonded area 1C can be obtained by subtracting the line segment data of labels L1,L3 from the overall line segment data (label data) (see spans SP1,SP2 in FIGS. 7B and 7C).

Next, as is shown in FIG. 8A, for example, measurement data may be obtained in a stepwise pattern. This indicates the occurrence of a cutting failure in the gap part of the corrugated cardboard blank 1. Namely, if a cutter deteriorates and its sharpness changes, a core part of the corrugated cardboard blank 1 may not be cut in specified dimensions, for example, as illustrated in FIG. 9 (see 1E). In such a case, measurement data similar to those shown in FIG. 8A occur. The above case means the existence of plural labels. Nonetheless, the line segment data of the bonded area 1C can be obtained by subtracting the line segment data of labels L1,L7 from the overall line segment data (label data) (see a span SP3 in FIG. 8A).

Further, as is illustrated in FIG. 8B, for example, measurement data may be partially cut off as indicated by labels L2,L4. Data similar to those shown in this diagram occur if the quantity of light is reduced due to oblique impingement or the like of a laser beam and no light can be detected as data on an image.

In the above case, the line segment data of the bonded area 1C can be obtained likewise by subtracting the line segment data of labels L1,L5 from the overall line segment data and hence taking into consideration portions failed to be detected on the image (see a span SP4 in FIG. 8B). Incidentally, as is illustrated in FIG. 8B, the positions of available data vary depending on the mounting position (direction) of the camera 11 (see labels L3,L3').

Further, the above-described values subtracted from the overall line segment data, that is, the individual line segment data of labels L1,L7 (FIG. 8A) and labels L1,L5 (FIG. 8B) are obtained in such a manner that their values become equal to the maximum value and the value next to the maximum value, respectively, of the label data (namely, L1 and L7 in FIG. 8A; and L1 and L5 in FIG. 8B).

Figure 10:
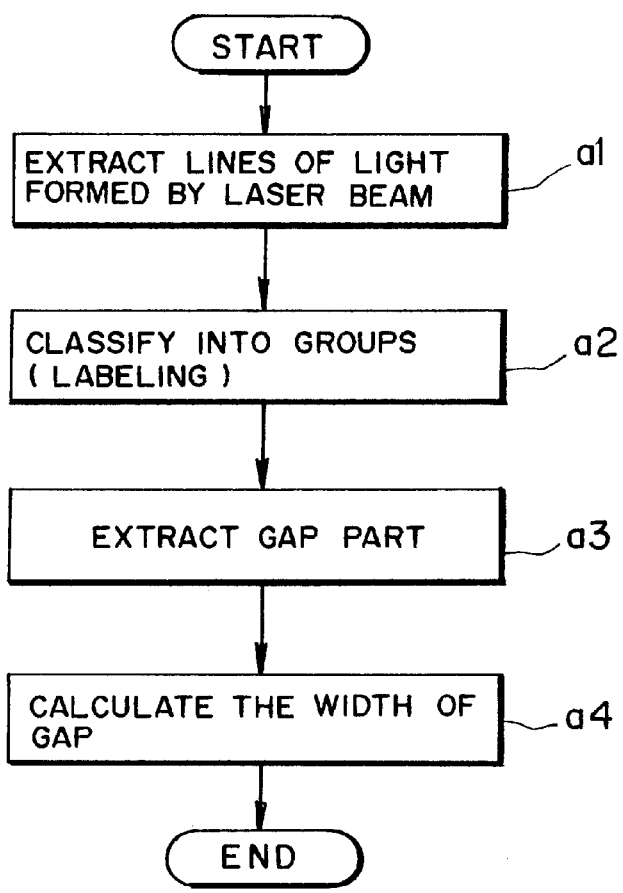
FIG. 10 is a flow chart for describing the first detection method shown in FIGS. 4A and 4B.

The system according to the embodiment of the present invention for the determination of the quality of the bonded area in the boxmaking blank is constructed as described above, and procedures of a quality determination by the system (i.e, the method according to the present invention for the determination of the quality of the bonded area in the boxmaking blank) is performed, for example, as shown in the flow chart of FIG. 10.

First, the positions of the light source 10 and camera 11 are adjusted by the positioning device 12 so that the light source 10 and the camera 11 are set at such positions as enabling them to irradiate light onto the bonded area 1C in each corrugated cardboard blank 1 travelling on and along the production line and to form an image of the bonded area 1C.

From the light source 10 toward the bonded area 1C, sheetlike light is then irradiated extending across the gap 1D, whereby an image of the bonded area 1C irradiated by the light from the light source 10 is formed. In other words, lines of light are extracted by such bi-level digitization as mentioned above (step a1).

Labeling processing is then applied to the thus-extracted lines of light to classify the resulting line segment data into groups (step a2). Described specifically, the classified line segment data can be obtained by using one of the two methods as described above. Based on the line segment data, the width of the gap 1D in the bonded area 1C is extracted (step a3).

Afterwards the thus-extracted width of the gap 1D is then compared with the preset upper limit and lower limit to determine whether the bonded area 1C is good or bad, the width of the gap 1D is calculated (step a4).

Two methods are available for the execution of the processing in these steps a3,a4, namely, for the determination of the width of the gap 1D in the bonded area 1C. These two methods will hereinafter be described in detail with reference to the flow charts of FIGS. 11 and 12.

Figure 11:
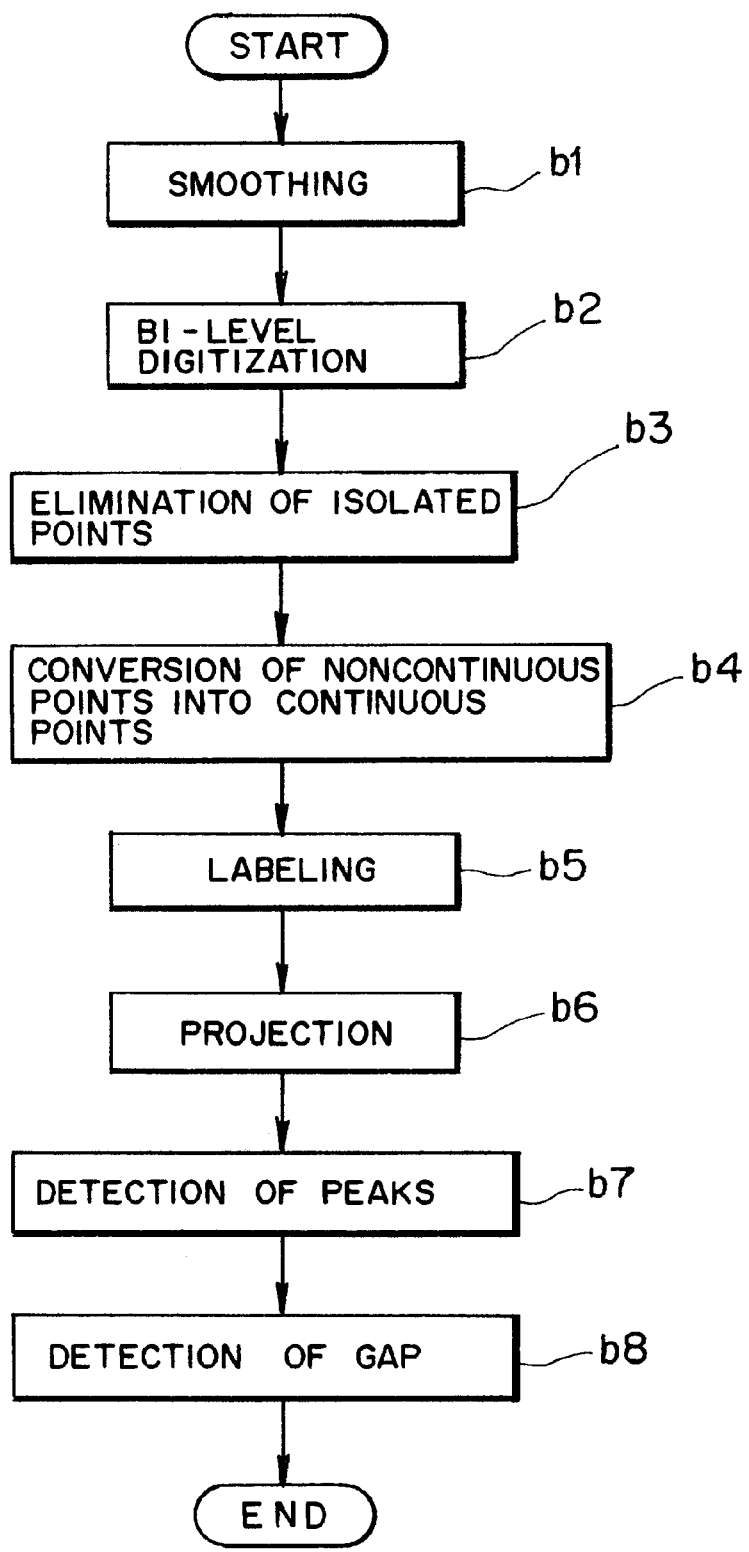
FIG. 11 is a flow chart for describing the second detection method shown in FIG. 5.

(a) Execution by the projection method:

A description will be made in accordance with the flow chart shown in FIG. 11. Upon initiation of a measurement, the black and white image of a monochrome image formed by the camera 11 is first subjected to smoothing (step b1), and bi-level digitization is conducted based on a preset threshold level as described above (step b2). As a result, the position of a line at which sheet-like light crosses a surface of a corrugated cardboard blank is extracted.

Subsequent to elimination of noncontinuous isolated points from the bi-level digitized data obtained by the bi-level digitization (step b3), continuation processing of noncontinuous points is performed (step b4). Referring to FIG. 4A, for example, the points $P_3,P_4$ which are noncontinuous with the point $P_1$ and the point $P_2$ are rendered continuous to form the line segment $P_3$–$P_4$. Labeling processing is then conducted on the line segment obtained by the continuation processing as described above. (step b5).

At this time, the bi-level digitized data are projected in X direction (step b6) and, from the results of the projection, the maximum peak $Y_p$ is searched, followed by the search for the peak $Y_g$ located at the position adjacent the maximum peak (step b7).

A $Y_g$ coordinate is then determined from the peak $Y_g$ and, from labeling data obtained beforehand, data close to the $Y_g$ coordinate is selected. The length of its line segment (the number of pixels) is then determined to detect the width of the gap of the bonded area (step b8).

Figure 12:
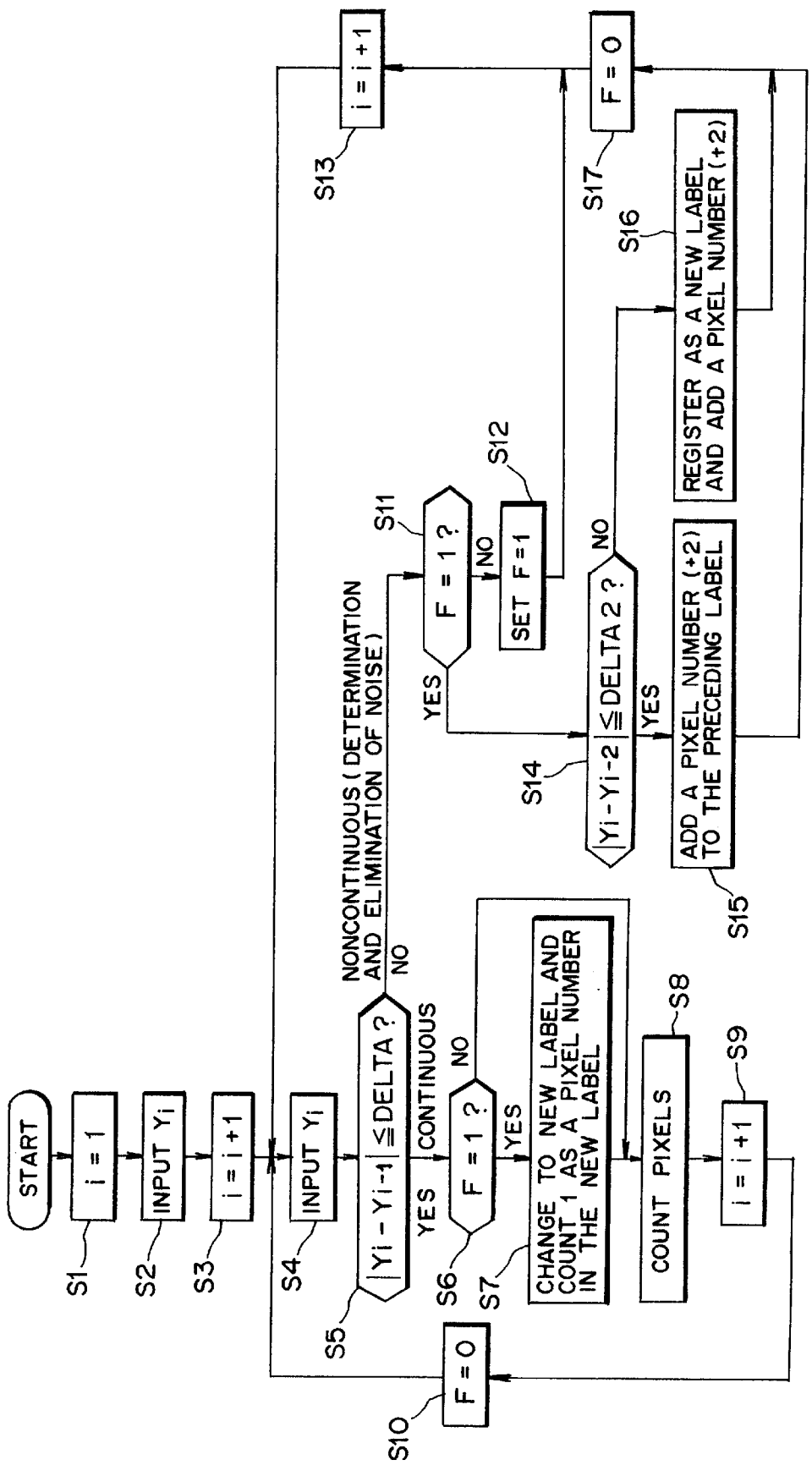
FIG. 12 is a flow chart for describing the algorism of the second detection method shown in FIG. 5.
Figure 13A:
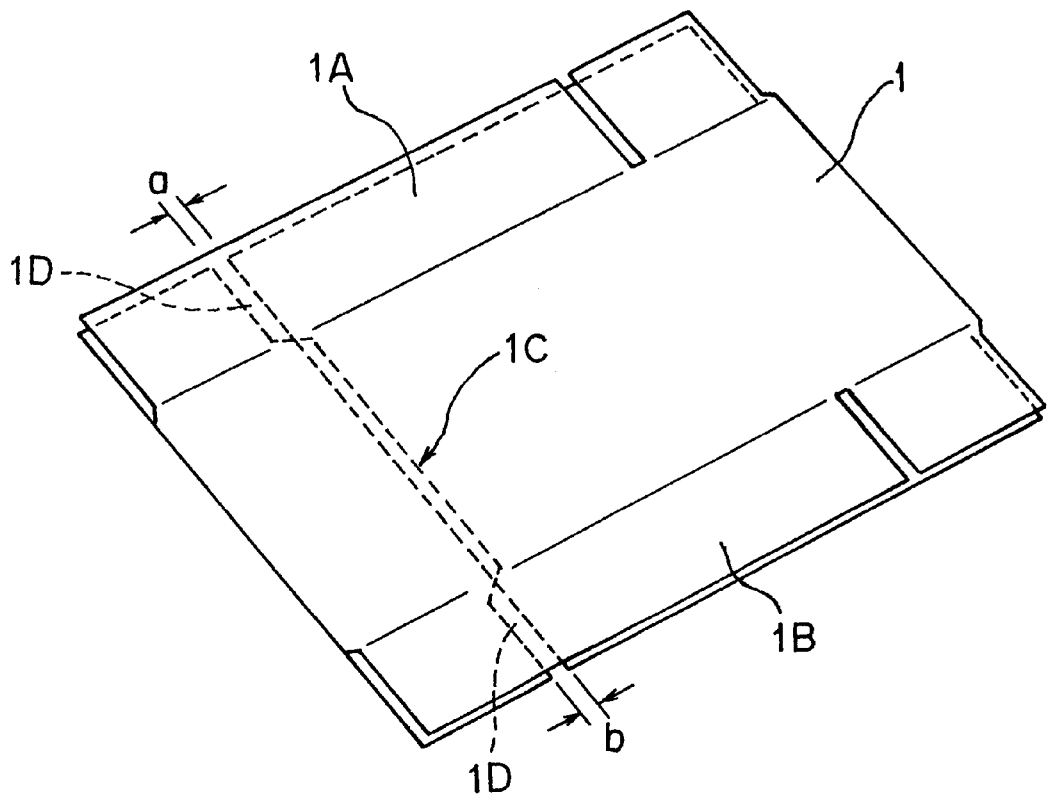
FIG. 13A is a schematic view showing a conventional corrugated cardboard box in a folded form.
Figure 13B:
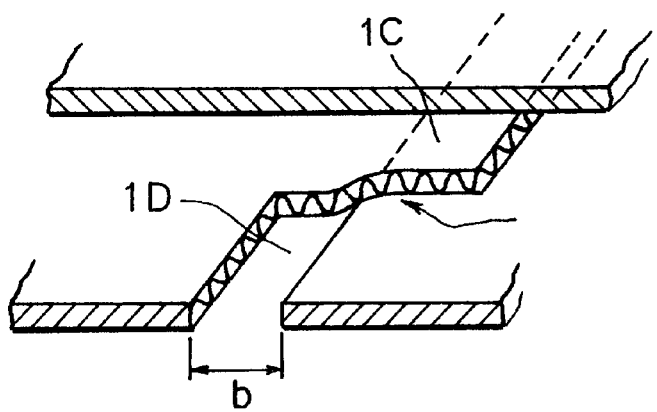
FIG. 13B is a partly cut-off fragmentary view of the conventional corrugated cardboard box of FIG. 13A.

(b) Execution by the sequential comparison method:

A description will be made in accordance with the flow chart shown in FIG. 12. Upon initiation of a measurement, with respect to i (pixel number)=1 (step S1), its distance $Y_1$ from the end of the image is inputted (step S2). Concerning i=2 (i=i+1) (step S3), $Y_2$ is then inputted (step S4). For the confirmation of continuity, a determination is next made as to whether or not the difference between $Y_1$ and $Y_2$ is not greater than a predetermined value ($|Y_i-Y_{i-1}| \leq$ DELTA?; step 5).

If the difference $(Y_i-Y_{i-1})$ is not determined to be greater than the predetermined value (the YES route from step S5) as a result, the existence of continuity is determined and a determination is then made as to whether or not a flag F has been set (F=1 ?; step S6). The flag F has 0 as its initial value but, when noncontinuity is determined, is changed to 1. Since no flag F has been set yet at a time point shortly after the initiation of the measurement (namely, F=0) (the NO route from step S6), pixels are simply counted (step S8) and then, i is incremented by 1 (step S9).

Subsequently, continuity with $Y_2$ is checked with respect to the next value, $Y_3$. If there is continuity, $Y_3$ is also registered in the same label (group) [the term "label" as used herein means the group of the first line segment ($f_1$ in FIG. 5)].

When i becomes, for example, equal to j (i=j), the following inequality is established: $|Y_i-Y_{i-1}|=|Y_j-Y_{j-1}|>$DELTA, resulting in determination of noncontinuity. The routine then advances along the NO route from step S5, and a determination is made as to whether or not this value $Y_j$ is a noise (subsequent steps S11 to S17).

Described specifically, a determination is first made as to whether or not the flag has been set (F=1?; step S11). Unless F=1 (the NO route from step S11), the flag F is set as F=1 (step S12).

Next, i is incremented by 1 (step S13), $Y_i=Y_{j+1}$ is inputted (step S4), and continuity is checked based on the difference, $Y_{j+1}-Y_j$ (step S5). If continuity is found to exist here (the YES route from step S5), a determination is made as to whether F=1 or not (step S6). If F=1, the label is then changed to a new label (the group of the second line segment) and 1 is counted as the number of pixel(s) in the new label (step S7). Subsequently, pixels are additionally counted (step S8) and, after i is incremented by 1 (step S9), F=0 is set (step S10).

If a lack of continuity is found (the NO route from step S5), a determination is again made as to whether F=1 or not (step S11). Since F=1 this time, the routine advances along the YES route from step S11 to step S14, and a determination is then made as to whether or not the difference between the current $Y_i$ value ($Y_i=Y_{j+1}$) and the second preceding value ($Y_{i-2}=Y_{j-1}$) is not greater than a predetermined value (DELTA2) ($|Y_i-Y_{i-2}|=|Y_{j+1}-Y_{j-1}| \leq$ DELTA2?; step S14).

If the determination results in YES (the YES route from step S14), $Y_j$ is determined to have occurred due to a noise and, assuming that the distance $Y_i$ of the second preceding pixel (i=j−1) still remains unchanged now (i=j+1), 2 is added as a pixel number to the preceding group (label) of the first line segment (step S15). After F=0 is set (step S17), i is incremented by 1 (step S13). Namely, if there is continuity with the second preceding data, the first preceding data is determined as a noise and is registered in the group (label) of the first line segment.

If the difference is found to be greater than predetermined value as a result of the determination in step S14 (the NO route from step S14), in other words, there is no continuity, the second preceding data does not have continuity either. This determination of noncontinuity is thus not interpreted as a determination of noncontinuity caused by a noise, and both of the data are registered as a new group (the group of the second line segment) different from the above-mentioned group and 2 is then added as a pixel number (step S16). After F=0 is set (step S17), i is incremented by 1 (step S13).

By these processing, the numbers of pixels in the first line segment ($f_1$ in FIG. 5), the second segment ($f_2$ in FIG. 5, which corresponds to the gap part), and the third or last line segment ($f_3$ in FIG. 5) can be determined. The width of the gap can then be determined by subtracting the numbers of the pixels in the first line segment and the third or last line segment from the total number of the pixels (a known value). As a consequence, the gap widths (SP1 to SP4) can be properly determined even if $Y_i$ data are as shown in FIGS. 7B and 7C and FIGS. 8A and 8B.

As has been described above, the method and system according to the present invention for the determination of the quality of a bonded area in each boxmaking blank conduct measurements by using a pattern of light no matter whether the measurements are made by the projection method or the sequential comparison method. Irrespective of the quantity level of light, the quality of the bonded area 1C of each corrugated cardboard blank 1 can therefore be determined. Further, owing to the use of strong light condensed in the form of a sheet as a light source, the quality of the bonded area of each corrugated cardboard blank 1 can also be determined easily without being affected by the color of a liner and/or printed parts of the corrugated cardboard blank 1. The method and system according to the present invention therefore have an advantage in that they can significantly improve the performance and reliability of a boxmaking production line of corrugated cardboard boxes.

In the above-described embodiment, the system is constructed for arrangement under the production line. It may however be constructed for arrangement above a production line. In such a construction, a similar advantage can be brought about. It is also possible to arranged two systems of the above-described construction, one above and the other under a production line. In this case, the quality of the bonded area 1C of each corrugated cardboard blank 1 can be determined no matter whether the bonded area 1C is on the upper side or on the lower side.

Further, in the above-described embodiment, each corrugated cardboard blank 1 is travelling with the width of the gap 1D in the bonded area 1C thereof directed at a right angle relative to the lengthwise direction of the production line. As an alternative, the corrugated cardboard blank 1 may be caused to travel with the width of the gap 1D of the bonded area 1C thereof directed in parallel with the lengthwise direction of the production line. In this alternative case, it is desired to arrange two systems of the above-described construction, one on one side of the production line and the other on the opposite side of the production line, so that they correspond to the gaps 1D in the top flap 1A and the bottom flap 1B, respectively.

Corrugated cardboard blanks are employed as boxmaking blanks in the above-described embodiment. However, the boxmaking blanks are not limited to such corrugated cardboard blanks. Further, the projection method or the sequential comparison method is used as an extraction method of the bonded area 1C. The extraction method is however not limited to such methods. The present invention can therefore be practiced by changing or modifying the above-described embodiment in various ways to such extent as not departing from the spirit of the present invention.

What is claimed is:

1. A method of determining the bonding quality of a bonded area of a flapped boxmaking blank in a boxmaking apparatus, which is disposed at an assembling station of a production line to assemble boxes from such boxmaking blanks one at a time by bonding opposite end portions of the individual boxmaking blank together, with confronting edges of companion end flaps defining a required gap, while the boxmaking blanks are conveyed on and along the production line successively through the boxmaking apparatus, in terms of the outline of the inter-flap gap, said method comprising the steps:

(a) irradiating sheetlike light onto the bonded area of the boxmaking blank being assembled such that said sheetlike light extends across said inter-flap gap;

(b) forming an image of the irradiated light as a light image line composed of discrete line segments which are arranged along a reference line for the flap edges of the gap and include at least one line segment located off said reference line;

(c) extracting from said light image line said line segment located off said reference line;

(d) computing a width of said inter-flap gap from a ratio of a length of said line segment to the entire length of said light image line; and (e) comparing the computed width of said inter-flap gap with a preset upper threshold and/or a preset lower threshold to thereby discriminate whether or not the opposite end portions of the boxmaking blank have been bonded in a correct posture.

2. The method of claim 1, wherein said sheetlike light to be irradiated is a laser light beam generated by a laser light source, and said forming of the light image line is carried out by an image pick-up device disposed at an angle with respect to the axis of said laser light beam from said laser light source.

3. The method of claim 2, further adjusting said laser light source and said image pick-up device in position with respect to the bonded area of the boxmaking blank having arrived at the assembling station of the production line.

4. The method of claim 1, wherein said computing of said width of said inter-flap gap is conducted by a projection method on said light image line.

5. The method of claim 1, wherein said computing of said width of said inter-flap gap is conducted by a sequential comparison method on said light image line.

6. A system for determining the bonding quality of a bonded area of flapped boxmaking blank in a boxmaking apparatus, which is disposed at an assembling station of a production line to assemble boxes from such boxmaking blanks one at a time by bonding opposite end portions of the individual boxmaking blank together, with confronting edges of companion end flaps defining a required gap, while the boxmaking blanks are conveyed on and along the production line successively through the boxmaking apparatus, in terms of the outline of the inter-flap gap, said system comprising:

(a) a light source, disposed at the assembling station of the production line, for irradiating sheetlike light onto the bonded area of the boxmaking blank being assembled such that said sheetlike light extends across said inter-flap gap;

(b) an image pick-up device, disposed at the assembling station of the production line with an angle with respect to the axis of a path of said sheetlike light from said light source, for forming an image of said sheetlike light as a light image line composed of discrete line segments which are arranged along a reference line for the flap edges of the gap and include at least one line segment located off said reference line; and (c) a computation and determination unit, operatively connected to said image pick-up device, for extracting from said light image line said line segment located off said reference line, computing a width of said inter-flap gap from a ratio of a length of said line segment to the entire length of said light image line, and comparing the computed width of said inter-flap gap with a preset upper threshold and/or a present lower threshold to thereby discriminate whether or not the opposite end portion of the boxmaking blank have been bonded in a correct posture.

7. The system of claim 6, further comprising a positioning device, operatively connected to said light source and said image pick-up device, for adjustably positioning said light source and said image pick-up device with respect to the bonded area of the boxmaking blank having arrived at the assembled station of the production line.

8. The system of claim 6, wherein said light source is a laser which generates a laser light beam, and said computation and determination unit executes the computation of said width of said inter-flap gap by a projection method on the basis of said light image line formed by said image pick-up device.

9. The system of claim 6, wherein said computation and determination unit executes the computation of said width of said gap by a sequential comparison method on the basis of said light image line formed by said image pick-up device.

10. The system of claim 6, wherein said light source and said image pick-up device are located both on one of upper and lower sides of the production line.

11. The system of claim 10, further comprising an additional light source identical with the first-named light source and an additional image pick-up device identical with the first-named image pick-up device, said additional light source and image pick-up device being located both on a side opposite to said first-named light source and image pick-up device with respect to the production line.

12. The system of claim 6, wherein said inter-flap gap across which said sheetlike light is to be irradiated extends transversely of a traveling path of the boxmaking blank on the production line.

13. The system of claim 6, wherein said inter-flap gap across which said sheetlike light is to be irradiated extends in parallel to a traveling path of the boxmaking blank on the production line.

* * * * *